United States Patent [19]

Nehring et al.

[11] 4,190,731
[45] Feb. 26, 1980

[54] PROCESS FOR WORKING UP DISTILLATION RESIDUES FROM THE HYDROFORMYLATION OF PROPENE

[75] Inventors: Rudolph Nehring; Manfred zur Hausen; Werner Neumann, all of Marl, Fed. Rep. of Germany

[73] Assignee: Chemische Werke Hüls AG, Marl, Fed. Rep. of Germany

[21] Appl. No.: 940,294

[22] Filed: Sep. 7, 1978

[30] Foreign Application Priority Data

Sep. 7, 1977 [DE] Fed. Rep. of Germany ....... 2740216

[51] Int. Cl.² .................................................. C07C 29/24
[52] U.S. Cl. .............................................................. 568/914
[58] Field of Search ................................................ 568/914

[56] References Cited

U.S. PATENT DOCUMENTS

| | | | |
|---|---|---|---|
| 2,595,096 | 4/1952 | Parker | 568/914 |
| 3,501,537 | 3/1970 | Johnson, Jr. et al. | 568/914 |
| 3,935,285 | 1/1976 | Tummes et al. | 568/914 |

*Primary Examiner*—Joseph E. Evans
*Attorney, Agent, or Firm*—Gilbert L. Wells

[57] ABSTRACT

The oxo process wherein propene is hydroformylated and then distilled to separate n-butyraldehyde, iso-butyraldehyde, n-butanol, iso-butanol, n-butyl formate, iso-butyl formate and distillation residues having an acid number of about 80 to 130 is improved by adding to the distillation residues molar to twice molar amounts, relative to the acid content, of n-butanol, isobutanol or mixtures thereof, carrying out an esterification in the presence of catalytically active amounts of sulphonic acids at temperatures from about 50° to 200° C., separating off the water of reaction, distilling the esterification reaction product and hydrogenating the distillate thereof.

8 Claims, 1 Drawing Figure

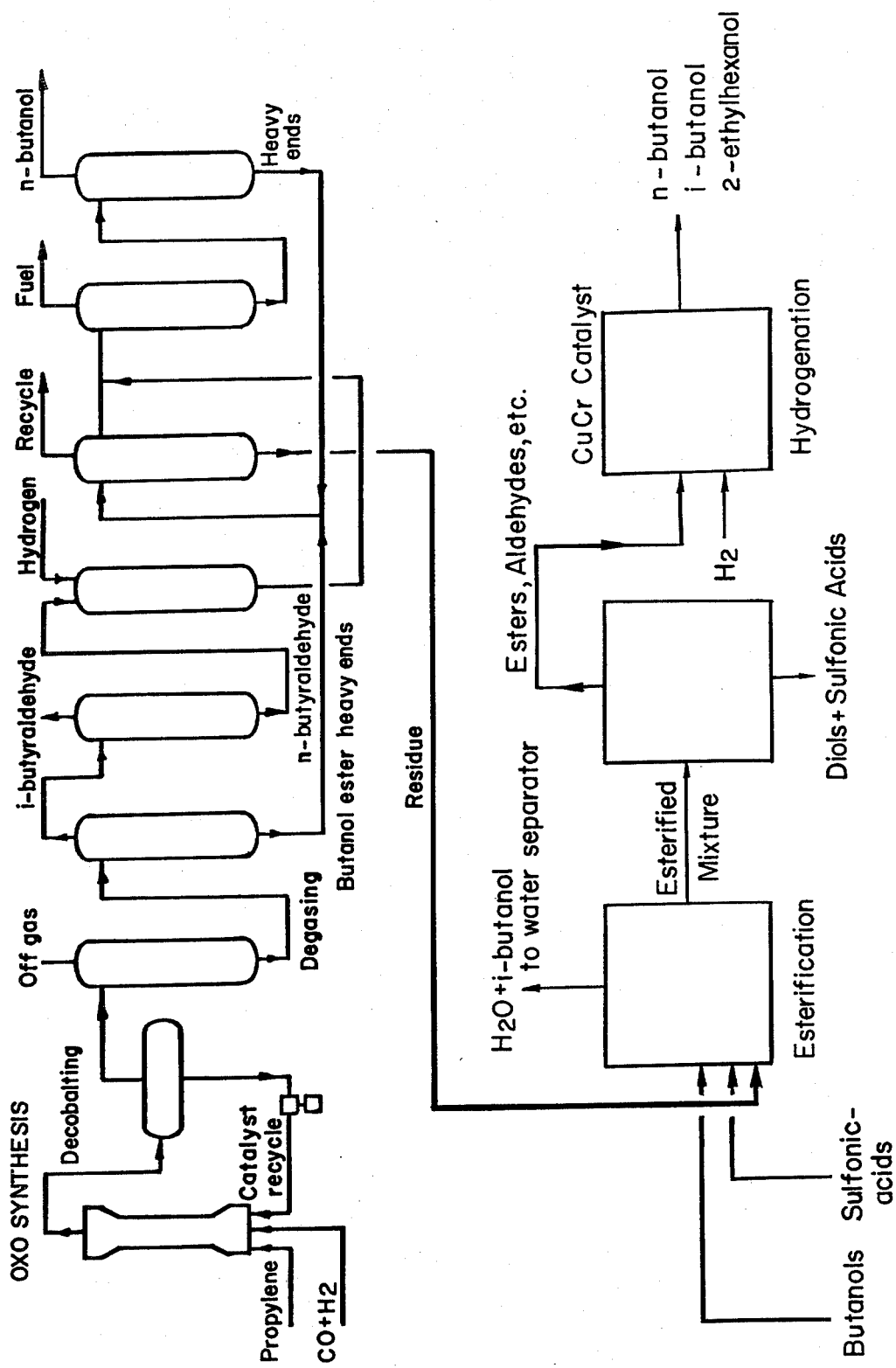

PROCESS FOR WORKING UP DISTILLATION RESIDUES FROM THE HYDROFORMYLATION OF PROPENE

BACKGROUND OF THE INVENTION

The field of the invention is the oxo process and the present invention is concerned with an improvement in the yield of the hydroformylation of propene.

The state of the art of the oxo process and the most pertinent improvements thereof may be ascertained by reference to the Kirk-Othmer "Encyclopedia of Chemical Technology" 2nd Edition, Vol. 14 (1967), pp. 373–390, particularly page 379 where it is indicated that propylene (propene) is used to produce butyraldehyde, pages 283–386 and FIG. 4 where hydroformylation and the steps of the oxo process are diagrammed and explained; German Published Application 2,460,784 and U.S. Pat. Nos. 3,501,537 and 4,048,233.

Kirk-Othmer, ibid, Vol. 8 (1966) discloses on page 794 that acid value or acid number is the number of milligrams of potassium hydroxide required to neutralize the free acids in one gram of a substrate.

The acid number of 1 is equivalent to 1.32 mg butyl alcohol.

In the large scale industrial hydroformylation of propene, especially in the presence of cobalt-catalysts, after separating off the n-butyraldehyde and iso-butyraldehyde and the by-products n-butanol and iso-butanol and n-butyl formate and iso-butyl formate by distillation, distillation residues are obtained which in general were hitherto burned. The residues contain, inter alia, n-butyric acid, iso-butyric acid, n-butyric-iso-butyl ester, iso-butyric n-butyl ester, n-butyric n-butyl ester, iso-butyric isobutyl ester, 2-ethylhexenal, 2-ethylhexanal, 2-ethylhexanol, n-butyraldehyde-di-n-butyl acetal and isomeric compounds and the monobutyrates and dibutyrates of 2-ethylhexane-1,3-diol and of 2-ethyl-4-methylpentane-1,3-diol.

The mixture consists of the isomeric butyric acids to the extent of up to 25%, of the butyl esters of butyric acid and butyrates of the dihydroxy compounds to the extent of up to 38% and of the isomeric butyraldehyde dibutyl acetals to the extent of about 10%.

Since in the case of hydroformylation processes carried out on a large industrial scale in general up to 5% of the crude hydroformylation product is obtained, during the distillation, as residues which cannot be utilized directly, there have been no lack of attempts to either refine them or to use them in an economically more favorable manner as a starting material for the production of the synthesis gas, olefin and hydrogen required in the hydroformylation process. According to U.S. Pat. No. 4,048,233, in order to manufacture a synthesis gas, the by-products and waste products of hydroformylation reactions are reacted at temperatures from 600° to 900° C. in the presence of steam and carbon dioxide on nickel-containing catalysts.

According to German Published Application 2,460,784, the esters obtained as by-products are saponified with sodium hydroxide solution or potassium hydroxide solution. The resulting alcohols are distilled off and the free carboxylic acid are obtained from the salts of the carboxylic acids by adding strong aqueous mineral acids. Since equivalent amounts of aqueous alkali and mineral acid are employed in this process, the raw material consumption of aqueous alkali and mineral acid is very high. The aqueous phase obtained contains organic compounds, in addition to large amounts of inorganic salts. This gives rise to high costs in the purification of the effluent.

It was known from U.S. Pat. No. 3,501,537 to hydrogenate the distillation residues from the hydroformylation with the aid of two catalyst beds arranged in series. The corrosiveness of these acid containing mixtures under the hydrogenation conditions, that is to say 230° to 255° C. and 70 to 700 bars, makes it necessary for the hydrogenation apparatus to be of expensive construction. Furthermore, under the energetic hydrogenation conditions claimed, after the addition reaction with hydrogen, acetals are more readily split into a mixture of butanol and butyl ehter than into butanol alone. In addition, the distillation carried out prior to the hydrogenation prevents utilization of high-boiling butyrates of dihydroxy compounds, which remain in the sump of the column and economic use thereof is therefore lost. Moreover, the life of the contact catalyst during the hydrogenation of non-pretreated acid/ester mixtures on only one catalyst is in general very low. Special measures and a significant technical effort are therefore necessary to increase the life of the catalyst.

SUMMARY OF THE INVENTION

Having in mind the limitations of the prior art, it is an object of the present invention to find a process which makes it possible to work up, in a simple and economic manner, the distillation residues from the hydroformylation of propene.

This object is achieved in an oxo process wherein propene is hydroformylated and then distilled to separate n-butyraldehyde, iso-butyraldehyde, n-butanol, iso-butanol, n-butyl formate, iso-butyl formate and distillation residues having an acid number of about 80 to 130, by adding to the distillation residues molar to twice molar amounts, relative to the acid content, of n-butanol, iso-butanol or mixtures thereof, carrying out an esterification in the presence of catalytically active amounts of sulphonic acids at temperatures from about 50° to 200° C., separating off the water of reaction, distilling the esterification reaction product and hydrogenating the distillate thereof.

BRIEF DESCRIPTION OF THE DRAWING

The FIGURE of the drawing is a schematic diagram of the present invention which shows the improvements over the oxo process shown in the flow diagram, page 135, Hydrocarbon Processing, Nov. 1977. The upper part of the illustration shows the prior art as shown by Hydrocarbon Processing, and the lower part, the improvement which constitutes the present invention. The residue from the prior art process is esterified with butanols using a sulfonic acid catalyst. Water is removed and the esterified mixture distilled to obtain the esters, aldehydes etc. which are then hydrogenated to obtain alcohols.

DESCRIPTION OF THE PREFERRED EMBODIMENTS

By esterification with excess n-butanol or iso-butanol in the presence of small amounts of acid catalysts, conversion of the mixture into products which, after distillation and hydrogenation, give only n-butanol, iso-butanol and 2-ethylhexanol is achieved, but no high demands must be made on the stability of the hydrogenation contact catalysts because of the substrate being free from acid. Under the conditions of the butyric acid esterification, not only are the butyrates of the dihydroxy compounds trans-esterified, butyric esters being formed, but the various acetals are split into butyraldehyde and butanol, butyraldehyde being converted into butanol in the subsequent hydrogenation.

The distillation residue from the hydroformylation of propene, which consists of esters, carboxylic acids, acetals and saturated and unsaturated aldehydes (actually about 17 compounds), which could be utilized industrially by customary methods only after troublesome separation with a high expenditure on distillation, can be converted almost quantitatively by the process according to the present inventon, in only two reaction steps and using known chemical-technical methods, into only three alcohols, which can be easily separated by distillation—in some cases particularly economically also together with the refined products (n-butanol, iso-butanol and 2-ethylhexanol) of the oxo synthesis—and have a wide field of application as plasticizer precursors or solvents.

The smooth course of the carboxylic acid esterification and of the acetal splitting under relatively mild conditions in one step in the presence of the same catalyst could not be foreseen. It was surprising that when sulphonic acids are used, esterification with n-butanol or iso-butanol is possible, avoiding elevated pressure; it already proceeds at temperatures which are automatically established through the boiling points of n-butanol or iso-butanol under normal pressure. If a relatively long column attachment is used, the esterification temperatures can be above the boiling temperatures.

The carboxylic acids contained in the distillation residue from the hydroformylation of propene indeed catalyze the esterification, but they necessitate temperatures of about 200° C., and this requires the use of a pressure apparatus. An acid number of about 10 can indeed be achieved after an esterification time of 4 hours without adding a catalyst, but the acetals are not split.

In the presence of 0.2% of p-toluenesulphonic acid, an esterification time of 3 hours is already sufficient to give an acid number of about 2 in an esterification apparatus operated under normal pressure. Suitable sulphonic acids, are, preferably, alkylbenzenesulphonic acids, such as, for example, dodecylbenzenesulphonic acid or cumenesulphonic acid, and naphthalenesulphonic acid. p-Toluenesulphonic acid is preferably employed. Surprisingly, a decrease in the catalytic activity, which can be caused by reaction of the sulphonic acid with one of the many possible reactants present in the residue, does not take place.

The esterification reaction can also be carried out in relatively large mixtures with short esterification times, that is to say economically, when 0.15 percent by weight of p-toluenesulphonic acid, relative to the distillation residue from the hydroformylation or propene, is added.

The remarkable catalytic activity of even small amounts of sulphonic acid can be explained by the joint action with the carboxylic acids present in the distillation residue, such as, for example, n-butyric acid and iso-butyric acid and in some cases formic acid in small amounts, which are to be regarded as co-catalysts. This "synergistic" effect could not be foreseen and in addition, known esterification catalysts, such as butyl titanate, zinc oxide, magnesium oxide and sodium aluminate, do not exhibit this property.

The process is restricted to n-butyl alcohol or iso-butyl alcohol as the esterification component because these alcohols are already contained in the oxo residue in the form of the butyl esters, and are formed from the butyl ester of butryric acid during the hydrogenation, and by using them no foreign substances are introduced. n-Butyl alcohol or iso-butyl alcohol can be employed individually or as a mixture.

The esterified mixture contains dihydroxy compounds, such as 2-ethylhexane-1,3-diol and 2-ethyl-4-methylpentane-1,3-diol, and the sulphonic acid used, which could shorten the life of the hydrogenation catalyst. The utilizable alcohols, esters and aldehydes can therefore be distilled off from the dihydroxy compounds and the added sulphonic acid in order to avoid damage to the hydrogenation catalyst. The resulting fractions can be hydrogenated quantitatively under a total pressure of up to 300 bars in the presence of copper chromite catalysts.

The sulphonic acids are employed in amounts of 0.1 to 2.0 percent by weight, relative to the distillation residue from the hydroformylation of propene and preferably 0.13 to 0.5 percent by weight is employed.

The esterification is carried out at a temperature from 50° to 200° C., preferably from 90° to 160° C., preferably under normal pressure and over a period of preferably 1 to 4 hours. During the esterification, the water of reaction formed is separated off.

The subsequent further processing, such as the distillation, takes place in a manner which is in itself known, as does the subsequent hydrogenation. The distillation is usually carried out under normal pressure, and can be accelerated under a slight vacuum; in particular, the distillation is carried out under reduced pressure so that valuable substances, such as the butyl esters of butyric acid, are separated off from the sump of the column as quantitatively as possible. The separation capacity of a column with 10 plates is adequate, and a reflux ratio of 2:1 does not need to be exceeded. Stirred kettles directly connected to or surmounted by a distillation column are particularly suitable.

The hydrogenation proceeds almost quantitatively, with little formation of by-products, under a total pressure of 300 bars in the presence of a fixed bed copper chromite catalyst of the Adkins type, which is composed of about 30% of CuO, 40% of $Cr_2O_3$ and 10% of BaO. Both aldehydes and esters, and unsaturated compounds, such as 2-ethylhexenal, are hydrogenated when this type of catalyst is used. Temperatures of 160° to 200° C. have proved particularly suitable when a trickle bed reactor, which makes it possible to process the product continuously, is employed. The three alcohols n-butanol, iso-butanol and 2-ethylhexanol, which have a broad application for the manufacture of plasticizers or as solvents, are obtained in a simple and economical manner and in a virtually quantitative yield.

EXAMPLE 1

The distillation residue from the hydroformylation of propene is mixed with 0.3 percent by weight of p-toluene-sulphonic acid and with a one molar excess of n-butanol (calculated according to the acid number of the oxo residue, which can vary between 80 and 130) and the mixture is heated to the boil on an attached column with a water separator under normal pressure until the acid number has fallen to a value of 1 to 2. As a rule, a reaction time of not more than 3 hours is adequate for this.

In order to separate off high-boiling constituents which cannot be used and which also contain the dissolved esterification catalyst, the mixture is distilled under normal pressure on a 25 cm long column provided with "Multifil" packing. The heat temperature should not exceed 190° C. (sump temperature up to 225° C.), in order to avoid a relatively large amount of high-boiling constituents being obtained. Under these conditions, the distillate contains less than 1 mg of sulphur/kg. When 1,200 g of oxo residue having an acid number of 120 are employed and are esterified with 380 g of n-butanol in the presence of 3.6 g of p-toluenesulphonic acid in the course of 3 hours down to an acid number of 1.8, a distillate (1,100 g) of the following composition (determined by gas chromatography) is obtained: 1.4% of first runnings, 1.5% of iso-butyraldehyde, 3.0% of n-butyraldehyde, 0.9% of iso-butyl alcohol, 18.2% of n-butanol, 0.6% of iso-butyric-isobutyl ester, 9.5% of iso-butyric-n-butyl ester, 4.8% of n-butyric-iso-butyl ester, 50.8% of n-butyric-n-butyl ester, 7.5% of 2-ethylhexanal and 1.8% of 2-ethylhexenal.

The mixture is then hydrogenated continuously on a copper chromite catalyst under 300 bars and at 180° C. 865 g of n-butanol, 98 g of iso-butanol and 92 g of 2-ethyl-hexanol are obtained.

EXAMPLE 2

37.6 metric of a distillation residue from the hydroformylation of propene having an acid number of 130 are mixed with 130 kg of 40% strength p-toluenesulphonic acid solution and with 12.9 metric tons of iso-butanol and are esterified in a stirred bulbous vessel under normal pressure down to an acid number of <2. The iso-butanol serves as an entraining agent for the water obtained (about 2.6 metric tons), which is discharged from the water separator. 36 metric tons of distillate are distilled off from the reaction mixture. According to analysis by gas chromatography, the distillate has the following composition: 2.0 percent by volume of iso-butyraldehyde, 3.2 percent by volume of n-butyraldehyde, 11.7 percent by volume of iso-butyl alcohol, 3.7 percent by volume of n-butyl alcohol, 0.4 percent by volume of intermediate runnings, 4.7 percent by volume of iso-butyric-iso-butyl ester, 2.0 percent by volume of iso-butyric-n-butyl ester, 36.6 percent by volume of n-butyric-iso-butyl ester, 19.3 percent by volume of n-butyric-n-butyl ester, 5.5 percent by volume of 2-ethylhexanal, 7.6 percent by volume of 2-ethylhexenal and 3.4 percent by volume of last runnings.

The mixture of this composition is continuously hydrogenated to n-butanol, iso-butanol and 2-ethylhexanol by known methods on copper chromite catalysts under an elevated pressure of hydrogen of 300 bars at 180° C. 15.4 metric tons of n-butanol, 12.2 metric tons of iso-butanol and 4.2 metric tons of 2-ethylhexanol are obtained.

EXAMPLE 3

500 g of a distillation residue from the hydroformylation having an acid number of 127 are mixed with 174 g of iso-butanol and 6 g of β-naphthalenesulphonic acid and the mixture is heated to the boil; the water which forms is discharged from a water separator. After an esterification time of just 2 hours, the acid number has become 2.5. The distillate, which has the composition indicated under Example 2, is hydrogenated according to the teachings in Example 2.

EXAMPLE 4

200 g of iso-butanol and 3 g of cumenesulphonic acid are added to 1,000 g of a distillation residue from the hydroformylation of propene having an acid number of 80 and the mixture is heated to the boil; the water which forms is removed via a water separater. After an esterification time of about 2.5 hours, an acid number of 2.4 is obtained, which falls to 1.4 after a further hour. The distillate, which has the composition indicated under Example 2, is hydrogenated according to the statements in Example 2.

EXAMPLE 5

364 g of n-butanol and 3 g of dodecylbenzenesulphonic acid are added to 1,000 g of a distillation residue from the hydroformylation of propene having an acid number of 128 and the mixture is heated to the boil; the water which forms is continuously removed from the water separater. After an esterification time of 4 hours, the acid number has become 2.5 and, after continuing the reaction, falls still lower. The composition of the distillate corresponds to the values indicated under Example 1. The mixture is hydrogenated according to the teachings in Example 1.

We claim:

1. In an oxo process wherein propene is hydroformylated and then distilled to separate n-butyraldehyde, iso-butyraldehyde, n-butanol, iso-butanol, n-butyl formate, iso-butyl formate and distillation residues having an acid number of about 80 to 130, the improvement comprising adding to the distillation residues molar to twice molar amounts, relative to the acid content, of n-butanol, iso-butanol or mixtures thereof, carrying out an esterification in the presence of catalytically active amounts of aryl or alkaryl sulphonic acids at temperatures from about 50° to 200° C., separating off the water of reaction, distilling the esterification reaction product and hydrogenating the distillate thereof with a copper-chromite catalyst to obtain n-butanol, isobutanol and 2-ethylexanol.

2. The process of claim 1, wherein said sulphonic acids are employed in an amount of about 0.1 to 2 percent by weight relative to the distillation residue.

3. The process of claim 1 wherein the esterification is carried out at temperatures from about 90° to 160° C.

4. The process of claim 2, wherein p-toluenesulphonic acid is employed as the sulphonic acid.

5. The process of claim 1, wherein said sulphonic acids are alkyl aryl sulphonic acids.

6. The process of claim 1, wherein said sulphonic acids are selected from the group consisting of dodecylbenzenesulphonic acid, cumenesulphonic acid, naphthalenesulphonic acid and p-toluenesulphonic acid.

7. The process of claim 1, wherein said sulphonic acids are employed in an amount of about 0.13 to 0.5 percent by weight relative to the distillation residue.

8. The process of claim 1, wherein said esterification is carried out to an acid number of about 1 to 2.

* * * * *